United States Patent [19]
Valet et al.

[11] Patent Number: 4,677,060
[45] Date of Patent: * Jun. 30, 1987

[54] PROCESS FOR DETERMINING THE PH VALUE IN THE INTERIOR OF A CELL

[75] Inventors: Günter Valet, Munich; Gerhard Ruhenstroth-Bauer, Gräfelfing; Erich Wünsch, Tutzing; Luis Moroder, Martinsried, all of Fed. Rep. of Germany

[73] Assignee: Max-Planck-Gesellschaft zur Foerderung der Wissenschaften E.V., Goettingen, Fed. Rep. of Germany

[*] Notice: The portion of the term of this patent subsequent to Mar. 5, 2002 has been disclaimed.

[21] Appl. No.: 680,078

[22] Filed: Dec. 10, 1984

Related U.S. Application Data

[63] Continuation of Ser. No. 346,094, Feb. 5, 1982, Pat. No. 4,503,148.

[30] Foreign Application Priority Data

Feb. 6, 1981 [DE] Fed. Rep. of Germany ....... 3104078

[51] Int. Cl.$^4$ .................. C12Q 1/02; C12Q 1/44; C12Q 1/38
[52] U.S. Cl. .................................. 435/29; 435/19; 435/23; 436/63; 436/163; 436/172
[58] Field of Search ................... 435/4, 29, 18, 19, 23, 435/24, 808, 291; 436/63, 163, 172, 800

[56] References Cited

U.S. PATENT DOCUMENTS 4,503,148 3/1985 Valet et al. ........................ 435/29

OTHER PUBLICATIONS

Visser et al, J. Histochem. Cytochem., 27(1): 32–35 (1979).
Thomas et al, Biochemistry, 18(11): 2210–2218 (1979).

Primary Examiner—Esther M. Kepplinger
Attorney, Agent, or Firm—John F. Witherspoon

[57] ABSTRACT

A process for determining the pH value in the interior of a cell is described. This is accomplished by measurement of the emission of a fluorescent substance which is absorbed by the cell through incubation in a solution. The solution contains a compound of the said fluorescent substance; the fluorescent substance is separated from this compound in the cell by an enzyme present in the cell. The fluorescent substance selected is one such that the frequency of the emission maximum is dependent on the pH value. The compound of this fluorescent substance which is selected is one which is membrane penetrating. Measurement of the fluorescence is based on the principle of measurement of the frequency at which the emission maximum occurs. A fluorescent substance suitable for this purpose is 2,3-dicyano-1,4-hydroquinone. A suitable membrane penetrating compound is 1,4-diacetoxy-2,3-dicyanobenzene or 1,4-dibutyryloxy-2,3-dicyanobenzene or 1,4-di(-tert-butyloxycarbonyl-1-alanyloxy)-2,3-dicyanobenzene.

3 Claims, 4 Drawing Figures

PROCESS FOR DETERMINING OF THE PH VALUE IN THE INTERIOR OF A CELL

This is a continuation of application Ser. No. 346,094 filed Feb. 5, 1982, now U.S. Pat. No. 4,503,148.

The invention relates to a process for determining the pH value in the interior of a cell through measurement of the emission of a fluorescent substance absorbed by the cell through incubation in a solution, the solution containing a compound of the fluorescent substance and the fluorescent substance of this compound being split in the cell by an enzyme present in this cell.

A process is known for measuring the pH value in the interior of a cell ($pH_I$) electrically by means of electrodes inserted into the cells. This process entails the disadvantage of partial destruction of the wall of the cell, inaccuracy of measurement, and application of a time-consuming process characterized by considerable complexity.

A process is also known for incubating cells, the pH value of which is to be measured, in solutions containing fluorescein esters. Free fluorescein does not penetrate the cell membrane. Esterified, nonfluorescent fluorescein, on the contrary, is membrane-penetrating. After it has penetrated the wall of the cell, the ester is split by enzymes present in the cell. This results in formation of the original, fluorescent fluorescein, which now cannot leave the cell and is therefore concentrated in the interior of the cell. The enzymes present in the interior of the cell which effect this separation (hydrolysis) are represented by esterases. The $pH_I$ is determined in this process by suspending cells in a physiological buffer solution containing a fluorescein ester in a photometric vessel and by illuminating this suspension alternately with two light sources of different excitation wavelength, measurement being simultaneously made of the intensity of the fluorescent light at the frequency of the emission maximum (Thomas et al., "Intracellular pH-Measurements in Ehrlich Ascites Tumor Cells Utilizating Spectroscopic Probes Generated in Situ," *Biochemistry*, Vol. 18, No. 11, pp. 2210-2218 (1979)). This process entails the disadvantage that no measurements can be performed for individual cells. Individual cell measurement is, however, of great importance, since a cell suspension may contain several types of cells with different $pH_I$ values which cannot be detected by the photometric vessel method.

A process is also known whereby measurements can be performed in a flow cytometer for cell suspensions treated with fluorescein esters in the manner described above (Visser et al., "Intracellular pH-Determination by Fluorescence Measurement," *The Journal of Histochemistry and Cytochemistry*, Vol. 27, No. 1, pp. 32-35 (1979)). In this process the fluorescence emission of individual cells is determined. In the flow cytometer the individual cells are excited by light of *one* wavelength. Since, however, the $pH_I$ can be determined only in measurement of the fluorescence at two excitation wavelengths when fluorescein esters are employed, two separate measurements must be performed for the same cell suspension (op. cit., p. 34, lefthand column, line 4, and p. 35, lefthand column, line 6). Hence, as with the photometric vessel process, only the mean value of the $pH_I$ of all the cells for which measurements are performed can be determined, since it is not possible to assign the measured values for the individual cell in the event of passage of the cell suspension through the flow cytometer twice.

It is the object of the invention to create a process and to prepare the substances required therefor, whereby the pH value can be determined in the interior of individual cells. This process is also to be suitable in particular for performance of measurements for entire cell populations in flow cytometers, so that corresponding distribution curves can be plotted in a simple manner, curves which in their turn open up fresh possibilities for diagnosis.

This object is achieved by selecting as the fluorescent substance one for which the frequency of the emission maximum depends on the pH value, and by employing as a compound of this fluorescent substance one which can penetrate the cell membrane, and further by determining, through measurement of the fluorescence, the pH-dependent frequency at which the fluorescence emission maximum occurs.

The essential feature of the invention thus lies primarily in the fact that there is selected as the fluorescent indicator a substance wherein the frequency rather than the intensity of the fluorescence depends on the pH value. This is to be construed as meaning that the frequency at which the emission spectrum has its maximum is pH-dependent. It is also important to cause this substance to be membrane-penetrating, so that it penetrates to the interior of the cell through the cell wall from the solution in which the cells are incubated. The initial substance is not suitable for this purpose. It is found, of course, that the formation of a derivative carried out to improve penetration yields a compound which itself does not fluoresce in the manner desired. It is thus necessary to initially employ a compound (i.e., derivative) of the fluorescent substance which is membrane-penetrating. The fluorescent substance is thereafter separated in the cell by an enzyme present in the cell in such a way that the pH-dependent fluorescent substance is obtained in the interior of the cell. Because of the inability of this fluorescent substance to penetrate the membrane, the latter can no longer leave the cell and accumulates in the interior of the cell, this providing the basis for measurement.

According to the invention one avoids the disadvantage of sequential intensity measurement of the fluorescence at two different wavelengths, such as is necessary in the case of fluorescein esters for $pH_I$ determination whereby $pH_I$ determination can be made only with cell suspensions and not with individual cells. This disadvantage is avoided by employing substances having a pH-dependent emission spectrum. The advantages are that the $pH_I$ can be determined in individual cells, only *one* excitation wavelength is required, and the measurement of the pH-dependent variations of the fluorescence emission maximum takes place *simultaneously*. This is accomplished by a process already known, whereby one simultaneously measures the intensity within the frequency range involved in two "light windows", such as between 420 and 440 and between 500 and 580 nm. The ratio of the two values is a gauge of the frequency of the fluorescence emission maximum, and the frequency in turn a gauge of the pH value. Since, however, the substances exhibiting these properties, in particular, for example, 2,3-dicyano-1,4-hydroquinone (DH), are not membrane-penetrating ones, it has not hitherto been possible to employ these substances on a larger scale for this purpose. If cells have been incubated in a solution of DH, the latter has not been able to penetrate through the cell walls to the interior of the cell and accumulate there. Nevertheless, in order to modify substances with the described frequency dependence of emission peaks so that they become capable of penetrating the cell membrane, the invention provides for derivative formation, that is, a conversion to a material which has the tendency to pass from a solution through the wall of a cell into the interior of the cell. This material must be a compound of the fluorescent substance which is capable of being split in the interior of the cell by the enzymes present therein in such a way that the original fluorescent substance is formed.

According to an advantageous additional development of the invention, 2,3-dicyano-1,4-hydroquinone (also: 2,3-dicyanohydroquinone) is used as such a fluorescent substance which fluoresces in the described pH-dependent manner. This substance is already known (see *CRC Handbook of Chemistry and Physics*, 54th Edition, page D-117; it is here designated in a different nomenclature as 3,6-dioxyphthalic dinitrile). This substance possesses the desired fluorescence properties. The emission maximum depends on the pH value. The additional advantage is afforded that the fluorescence occurs in a frequency range essentially different from the one in which other fluorescences of importance for analytical purposes occur (such as ones of importance in determination of the DNA concentration). Thus, in this way it is possible to simultaneously measure not only the fluorescence which is important in the pH determination but also other fluorescences, and consequently measure more than one parameter.

One possibility of achieving membrane penetrability is represented by acylation. An example of this is esterification, in which case esterases present in a cell cleave the indicator by hydrolysis after the ester has penetrated the wall of the cell and thereby render it effective.

For example, esterification with acetic acid yields the compound 1,4-diacetoxy-2,3-dicyanobenzene (DDB) in the case of 2,3-dicyano-1,4 -hydroquinone. If cells are incubated in a solution of DDB, they absorb this substance rapidly and extensively. 2,3-dicyano-1,4-hydroquinone is produced in the cell again as a result of hydrolysis. It is found that the DH obtained by hydrolysis from DDB in the cell and in the solution possesses approximately twice the operating range previously known, apparently because the phenolic structure of the compound in the interior of the cell and in the solution responsible for the fluorescence activity cannot be decisively modified by oxidation. While it has hitherto been assumed that a pH dependence of fluorescence occurs in the case of 2,3-dicyano-1,4-hydroquinone only between pH=6 and pH=8, it is found in the process claimed for the invention to occur between pH=3 and pH=9, that is, for all values of importance in biochemistry.

As its name indicates, the structure of 1,4-diacetoxy-2,3-dicyanobenzene is such that an acetoxy group is present in the first and fourth positions of the benzene ring, and a cyano group in the second and third positions. The fifth and sixth positions are occupied by H atoms. However, the invention also includes substances in which these positions are occupied by other groups (including bonding of additional benzene rings) whereby the activities in question (fluorescence after hydrolysis in the cell; good migration into the cell) are not eliminated or are even intensified.

Butyric acid or an N-shielded amino acid may also be employed in place of acetic acid for the purpose of acylation of the hydroquinone. The following substances, believed to be new, are then obtained: 1,4-dibutyryloxy-2,3-dicyanobenzene or 1,4-di(-tert-butyloxycarbonyl-1-alanyl-oxy)-2,3-dicyanobenzene as membrane penetrating compounds of 2,3-dicyanohydroquinone.

In its general form this process also makes it possible to ascertain the concentration and kinetics of enzymes in individual compartments of a cell. For this purpose transport through the wall of the cell is effected by coupling a group which is separated only by one enzyme in a specific compartment of the cell. Hence fluorescence occurs only in places inside the cell at which this enzyme is present.

An example of an embodiment of the invention is described in detail in what follows, with reference to the accompanying drawings, in which FIG. 1 shows the excitation spectrum of 2,3-dicyano-1,4-hydroquinone (DH);

The initial substance is the fluorescent substance 2,3-dicyano-1,4-hydroquinone (DH) having the following structural formula:

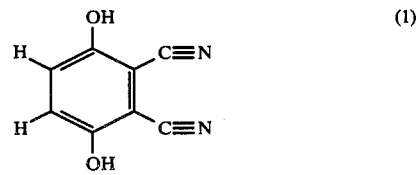

(1)

3.2 g of freshly crystallized DH are mixed in 30 ml $H_2O$ + 2.4 g NaOH in an atmosphere of argon at 0° C. with 4.7 ml acetic anhydride. The rapidly deposited precipitate is filtered off after four minutes, washed with water, and dried. After drying in a vacuum, the precipitate is recrystallized from ethanol. With the initial quantities indicated, the yield amounts to 3.09 g. 1,4-diacetoxy-2,3-dicyano benzene $C_{12}H_8N_2O_4$ (DDB) is thereby obtained. It has the following structural formula:

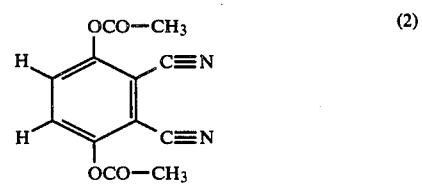

(2)

The reaction which has been described proceeds as follows:

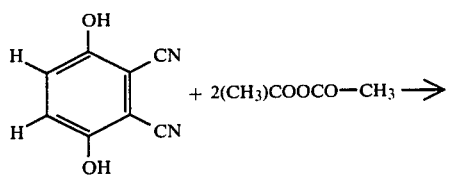
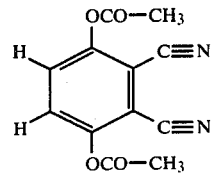

(3)

The reaction is an acetylation.

The DDB obtained as a result of this reaction has a melting point of 165° to 167° C. It is chromatographically pure in dichloroethane/heptane/methanol 90:10:5. The following analysis is obtained:

C 59.02 H 3.30 N 11.47 theoretical
C 58.95 H 3.33 N 11.48 actual

A solution of DDB is produced in the following manner:

1 mg DDB is dissolved in 1 ml DMSO (dimethylsulfoxide).

A cellular suspension suitable for measurement is produced in the following manner:

250 μl of a cellular suspension in a concentration of $1 \times 10^7$ cells/ml in a 0.95% solution of table salt, brought to pH=7.4 with 10 mMol trishydroxymethylaminomethane/HCl, are added to 5 μl of the DDB solution. This corresponds to a concentration of 20 μg DDB substance per ml cellular suspension.

The cellular suspension containing DDB is incubated for 10 minutes at room temperature.

The cellular suspension is then introduced into the cell supply container of a flow cytometer and the fluorescence of the individual cells is measured in two light windows.

Figure 1:
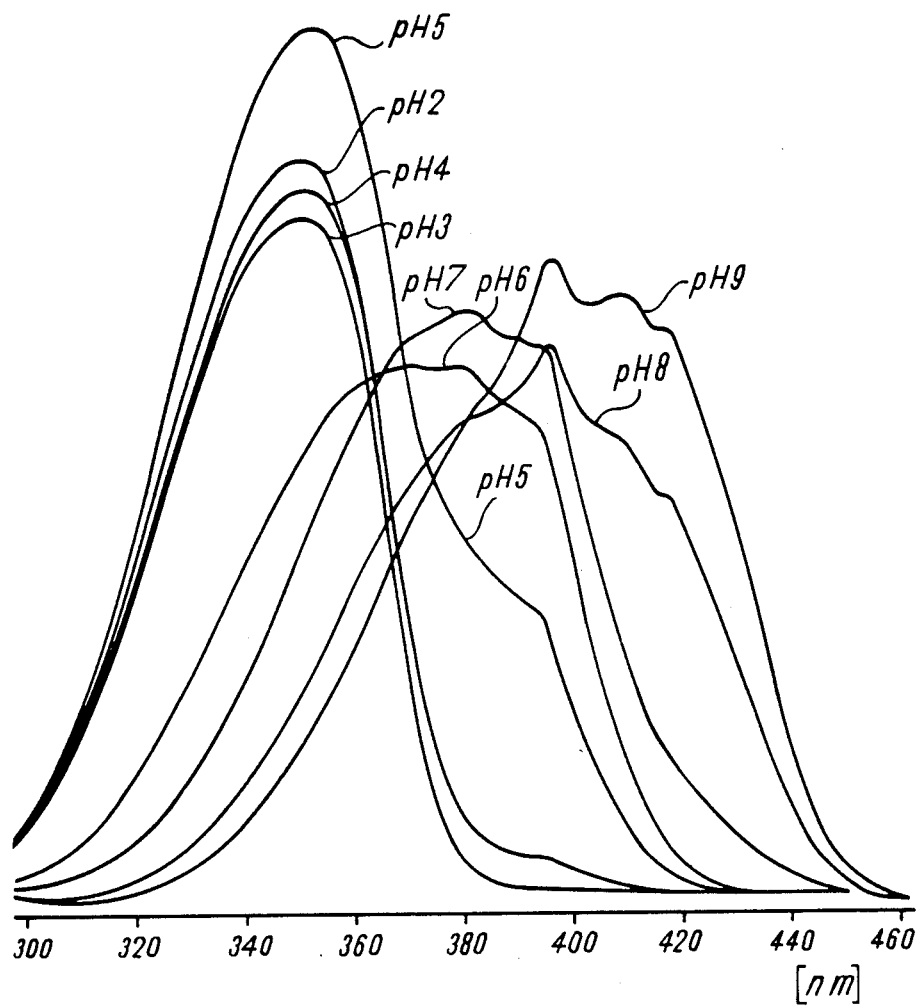

The fluorescence of the individual cells can be excited within the 300–410 nm range in keeping with the spectra shown in FIG. 1. Emission spectra are obtained in the process for the substance which has in the meantime been hydrolyzed and accumulated in the interior of the cell, namely for the 2,3-dicyanohydroquinone, these spectra being similar to those in FIG. 2, which were measured in a free solution. It is to be seen that the position of the maxima is definitely dependent on the pH value.

Owing to the good membrane penetrability of the DDB, the amount of DDB and the rate of penetration depend on the difference in the concentrations of this substance outside and inside the cell. But since the DDB penetrating the cell is hydrolyzed (split) to DH by enzyme inside the cell, a concentration gradient persists for DDB so long as the solution in which the cells are incubated still exhibits a significant concentration of DDB. The period of 10 minutes indicated in the foregoing discussion of the experimental conditions is wholly adequate for concentration in the cell of an amount of DH sufficient for measurement of the fluorescence.

Figure 2:
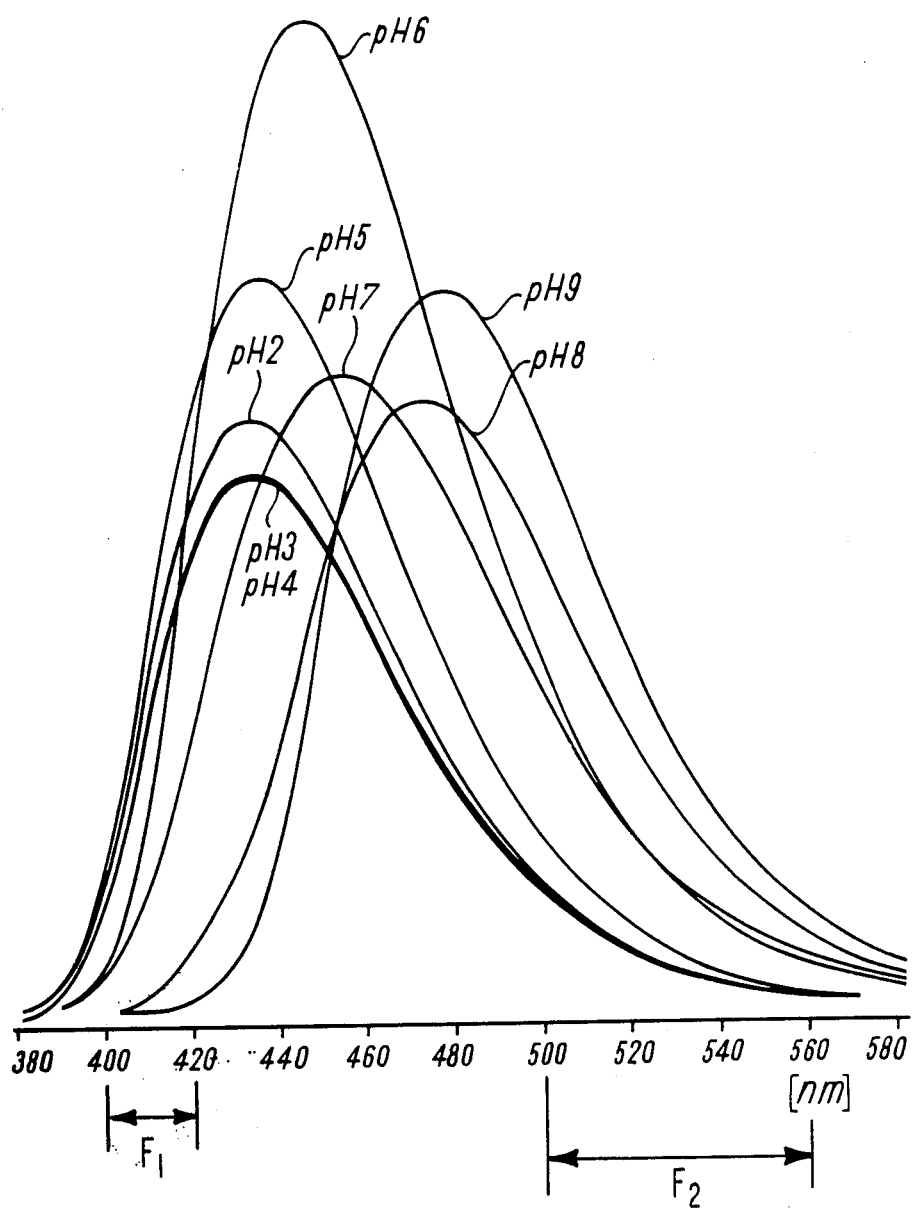
FIG. 2 shows the emission spectrum of 2,3-dicyano-1,4-hydroquinone (DH)

The displacement shown in FIG. 2 of the emission spectra maxima at different $pH_I$ values is determined by the test method of measuring the fluorescence in two "light windows" and forming the quotient of the measured values. These two "light windows" have been entered in FIG. 2, they being designated as $F_1$ and $F_2$.

The quotient of the two measured values is in the case of the typical curve traces shown a gauge of the position of the maximum and thus to be directly related to the $pH_I$ value. There is no need for further discussion of the details of this measurement process, since they are familiar to the specialist.

Figure 3:
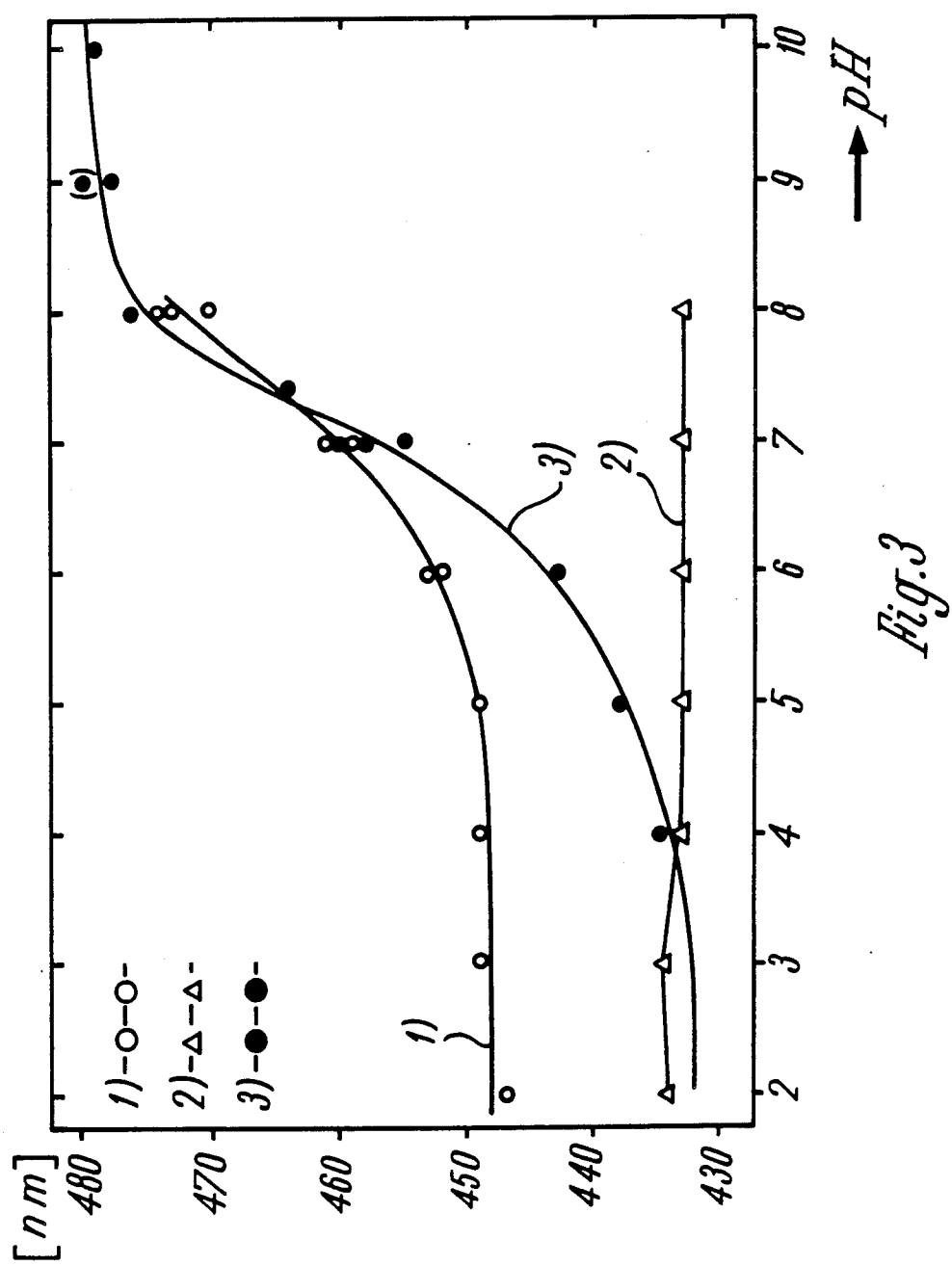
FIG. 3 shows the frequency dependence of the position of the fluorescence maximum for DH, DDB, and DH after hydrolysis in the cell.

The dependence of the frequency, at which the emission spectrum maximum occurs, on the pH value is shown in FIG. 3. Three curves have been plotted in the drawing. The first curve (represented by small circles) illustrates the dependence of the emission peak wavelength for the original substance DH prior to esterification and prior to penetration to the interior of the cell. Between pH 5.5 and pH 8 there is to be discerned an approximately linear rise which shows the suitability of the substance for such a measurement.

Curve 2 (small triangles) shows the measurements for the esterified substance DDB which penetrates to the interior of the cell. As is to be seen, esterification causes the emission spectrum and the position of the peaks to be independent of the pH value.

Curve 3 (dots) illustrates the measurement after penetration of DDB into the cell and reconstitution of DH by hydrolysis. It shows again the dependence of the frequency, at which the emission peak occurs, on the pH value and—something which is especially surprising—in a substantially wider operating range, namely, between pH 3 and pH 9. As has already been pointed out, this is probably to be ascribed to the fact that, when DH is produced in the cell from DDB through hydrolysis, partial ineffectiveness of DH caused when the OH groups of DH (in position 1 and position 4) responsible for fluorescence are again partly oxidized does not immediately occur.

The alternatively applicable membrane penetrating compounds of DH which are mentioned in the foregoing are produced as follows:

(a) 1,4-dibutyryloxy-2,3-dicyanobenzene:

4.1 ml butyric acid anhydride are added to 1.6 g 2,3-dicyanohydroquinone in 30 ml 1N NaOH. After agitation for 15 minutes, the mixture is diluted with water, and the reaction mixture is extracted with acetic acid. The separated organic phase is washed in succession with 0.1N NaOH and water and evaporated in a vacuum. The residue is recrystallized from ethanol. Yield 2.3 g (77% of theoretical value). Melting point 86°–87° C.

$C_{16}H_{16}N_2O_4$ (300.3):
Theoretical: C: 63.9, H: 5.37, N: 9.33.
Actual: C: 64.0, H: 5.38, N: 9.34.

The 1,4-dibutyryloxy-2,3-dicyanobenzene has the following structural formula:

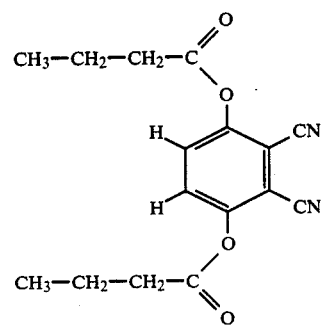

(b) 1,4 di(-tert-butyloxycarbonyl-alanyl-oxy)-2,3-dicyanobenzene 4.7 g tert-butyloxycarbonyl-l-alanine and 1.6 g 2,3-dicyanohydroquinone are mixed in 100 ml acetic acid cooled by iced water with 5.2 g dicyclohexylcarbodiimide. After agitation for 12 hours, the precipitated urea is filtered off, the filtrate is evaporated in a vacuum, and the residue is recrystallized from ethanol. Yield 4.2 g (84% of theoretical value). Melting point 164°–167° C. (decomposition).

$C_{24}H_{30}N_4O_8 \cdot H_2O$ (520.52):

Theoretical: C: 55.38, H: 6.20, N: 10.76.

Actual: C: 55.34, H: 6.12, N: 10.80.

The 1,4 di-(tert-butyloxycarbonyl-alanyloxy)-2,3-dicyanobenzene has the following structural formula:

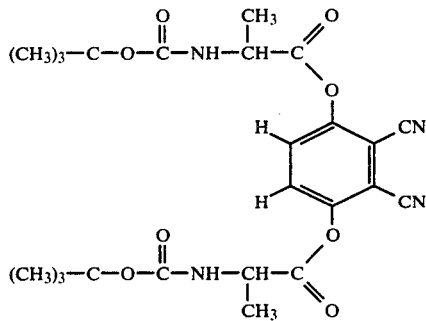

Figure 4:
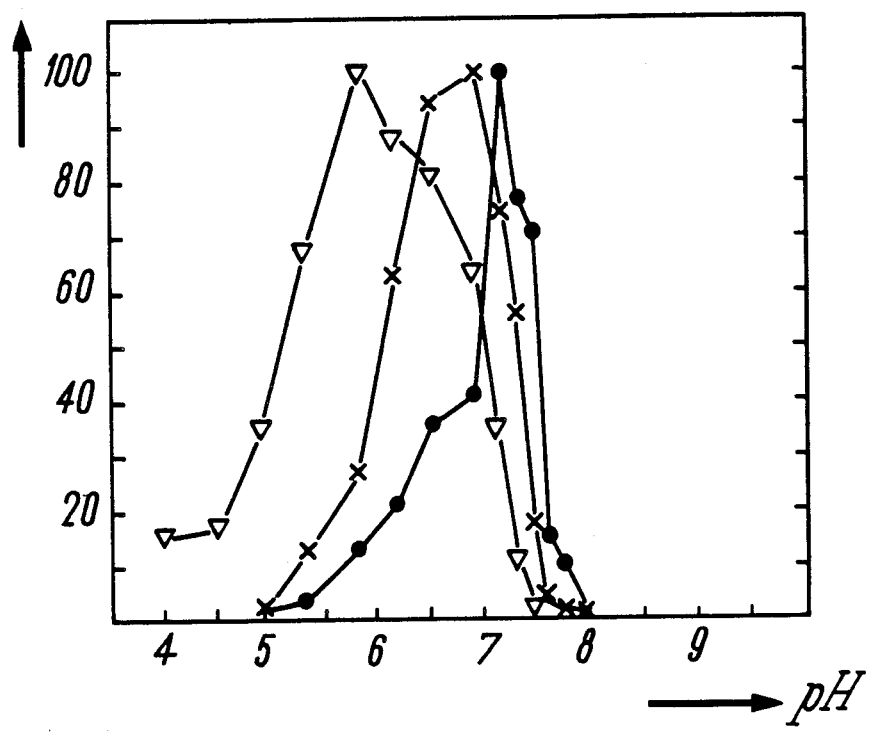
FIG. 4 shows several pH distributions measured by the process claimed for the invention.

FIG. 4 illustrates the diagnostic value of measurement of the $pH_I$ value for a cell population. In this figure there are three distribution curves, Curve 1 (solid dots) for healthy bone marrow cells of rats, Curve 2 (small crosses) for Ehrlich Ascites tumor cells, and Curve 3 (small triangles) for human ovarian cancer cells.

As is to be seen, the pH distribution curve of the cell population is distinctly different for all three types. The measurement of such pH-distribution curves of individual cells is made possible only by the process according to the invention. New paths are thereby opened up for diagnosis.

What is claimed is:

1. A process for determining the pH in the interior of a cell which comprises simultaneously measuring at two wavelengths the emission from a single excitation of a fluorescent substance within said cell, said substance having an emission maximum which is pH dependent.

2. The process as defined in claim 1 wherein said fluorescent substance is 2,3-dicyano-1,4-hydroquinone or 2,3-dicyano-1,4-hydroquinone having substituents in the fifth and/or sixth position of the benzene ring.

3. The process as defined in claim 1 wherein said fluorescent substance is 2,3-dicyano-1,4-hydroquinone.

* * * * *